US009834797B2

(12) United States Patent
Stowers et al.

(10) Patent No.: US 9,834,797 B2
(45) Date of Patent: Dec. 5, 2017

(54) FERMENTATION BASED ON HYDROLYZED CORN AND/OR SUGAR CANE MASH TO PRODUCE PROPIONIC ACID

(71) Applicant: Dow Global Technologies LLC, Midland, MI (US)

(72) Inventors: Christopher C. Stowers, Carmel, IN (US); Brandon A. Rodriguez, Houston, TX (US); Brad M. Cox, Fishers, IN (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/760,321

(22) PCT Filed: Feb. 17, 2014

(86) PCT No.: PCT/US2014/016659
§ 371 (c)(1),
(2) Date: Jul. 10, 2015

(87) PCT Pub. No.: WO2014/158432
PCT Pub. Date: Oct. 2, 2014

(65) Prior Publication Data
US 2016/0017384 A1   Jan. 21, 2016

Related U.S. Application Data

(60) Provisional application No. 61/806,081, filed on Mar. 28, 2013.

(51) Int. Cl.
*C12P 7/52*   (2006.01)

(52) U.S. Cl.
CPC ............. *C12P 7/52* (2013.01); *C12P 2203/00* (2013.01)

(58) Field of Classification Search
None
See application file for complete search history.

(56) References Cited

U.S. PATENT DOCUMENTS

| 1,932,755 | A | 10/1933 | Stiles et al. | |
|---|---|---|---|---|
| 5,563,069 | A | 10/1996 | Yang | |
| 2004/0087808 | A1* | 5/2004 | Prevost | C12P 7/06 554/9 |
| 2007/0014905 | A1* | 1/2007 | Chen | A23J 1/125 426/490 |
| 2008/0053611 | A1 | 3/2008 | Neil | |

FOREIGN PATENT DOCUMENTS

| WO | 2009/154624 A1 | 12/2009 |
|---|---|---|
| WO | 2011/029166 A1 | 3/2011 |

OTHER PUBLICATIONS

Free Dictionary. Corn mash. www.thefreedictiionary.com/Corn+mash. Accessed Sep. 22, 2016. p. 1-5.*
Atsumi, S. and Liao, J.C. Appl. Environ. Microbiol. (2008) 74:7802-7808.
Barbirato, F., Chedaille, D., Bories, A., "Glucose/glycerol co-fermentation: One more proficient process to produce propionic acid by Propionibacterium acidipropionici," 1997 Appl. Microbiol. Biotechnol. 47, 441-446.
Berríos-Rivera SJ, San K-Y, Bennett GN. (2003). J. Ind. Microbiol. Biotechnol. 30, 34-40.
Boyaval, P., Corre, C., "Production of propionic acid," Lait. (1995) 75: 453-461.
Carta, F.S., Soccol, C.R., Ramos, L.P., Fontana, J.D., Bioresour. Technol. (1999) 68, 23-28.
Chen, X.S., Ren, X.D., Dong, N., Li, S., Li, F., Zhao, F.L., Tang, L., Zhang, J.H., Mao, Z.G. Bioprocess. Biosyst. Eng. (2012) 35, 469-475.
Coral, J., Karp, S.G., Porto De Souza Vandenberghe, L., Parada, J.L., Pandey, A., Soccol, C., "Batch fermentation model of propionic acid production of Propionibacterium acidipropionici in different carbon sources," 2008 Appl. Biochem. Biotechnol. 151, 333-341.
Cousin, F. J., Jouan-Lanhouet, S., Dimanche-Boitrel, M.T., Corcos, L., Jan, G. (2012). PLoS One. 7, e31892.
Da Silva, G. P., Mack, M., Contiero, J. Biotechnol. Adv. (2009) 27, 30-39.
Feng, X., Chen, F., Xu, H., Wu, B., Li, H., Li, S., Ouyang, P. "Green and economical production of propionic acid by Propionibacterium freudenreichii CCTCC M207015 in plant fibrous-bed bioreactor," 2011 Bioresour. Technol. 102, 6141-6146 XP028407882.
Choojun, S., et al. "Improvement of propionic acid production for antifungal activity from whey by calcium alginate immobilization of Propionibacterium acidipropionici TISTR 442," 2012 J. Agric. Sci. Tech. A 2 863-872.
Eden A., Van Nedervelde L., Drukker M., Benvenisty N. and Debourg A. Appl. Microbiol. Biotechnol. (2001) 55:296-300.
El-Samragy YA, Khorshid MA, Foda MI and Shehata AE. Int. J. Food Microbiol. (1996) 29:411-416.
Faye T, Asebø A, Salehian Z, Langsrud T, Nes IF and Brede DA. Appl. Environ. Microbiol. (2008) 74:3615-3617.
Yu Liang Huang, et al: "Production of carboxylic acids from hydrolyzed corn meal by immobilized cell fermentation in a brous-bed bioreactor", Bioresource Technology, vol. 82, No. 1, Jan. 1, 2002, pp. 51-59. XP055120987.
Rathin Datta: "Acidogenic fermentation of corn stover," Biotechnology and Bioengineering, vol. 23, No. 1, Jan. 1, 1981, pp. 61-77, XP055121002.
Yang, S-T., Huang Y., Hong G., "A novel recycle batch immobilized cell bioreactor for propionate production from whey lactose," Biotechnol. Bioeng. (1995) 45:379-386.

(Continued)

*Primary Examiner* — Paul J Holland
(74) *Attorney, Agent, or Firm* — Dinsmore & Shohl LLP

(57) ABSTRACT

A process to prepare propionic acid comprises preparing a fermentation broth of water; at least 30 weight percent hydrolyzed corn mash solids, hydrolyzed sugar cane mash solids, or a combination thereof, based on the combined weight of the fermentation broth as a whole; and *propionibacteria*; without including the typical, frequently very costly supplementation with vitamin and mineral packages. Surprisingly, these mash solids, which must often be disposed of following syrup production, are capable of supplying the nitrogen, micronutrients, vitamins and minerals known to be needed for *propionibacteria* fermentation, making their sole or significant use as fermentation mediums far more economical and therefore desirable than other fermentation mediums which require supplementation.

15 Claims, 6 Drawing Sheets

(56) References Cited

OTHER PUBLICATIONS

Zhang, A. and Yang, S-T., "Engineering of Propionibacterium acidipropionici for enhanced propionic acid tolerance and fermentation," Biotechnol. Bioeng. (2009) 104, No. 4: 766-773.
PCT/US2014/016659, International Search Report & Written Opinion of the International Searching Authority dated Jun. 12, 2014.
PCT/US2014/016659, International Preliminary Report on Patentability dated Jul. 23, 2015.
PCT/US2014/016659, Response Written Opinion dated Jan. 28, 2015.

* cited by examiner

FERMENTATION BASED ON HYDROLYZED CORN AND/OR SUGAR CANE MASH TO PRODUCE PROPIONIC ACID

This application claims the benefit of U.S. Provisional Patent Application Ser. No. 61/806,081, filed on Mar. 28, 2013, which is incorporated herein by reference in its entirety.

The invention relates to the field of fermentations to produce propionic acid as a product. More particularly, it relates to use of hydrolyzed corn mash or hydrolyzed sugar cane mash as viable and economically-advantaged fermentation substrates.

It is well-recognized that there is a need for processes to efficiently convert renewable carbon-containing materials, such as biomass, into products in such a manner that the energy, carbon and mass content of the materials are efficiently transferred into such products. Many of these processes use sugars, such as glucose or sucrose, that are obtained by enzymatic, acid, base, or chemo-mechanical hydrolysis from previously processed agricultural grains, including corn, sugar cane, wheat and soy. These sugars have generally been purified, through filtration or crystallization, to form liquid syrups or crystallized solids of desirable purity and concentration. The purified sugars are then used as the carbon source in fermentations to yield products such as propionic acid.

For example, US Publication 2008053611 (WO 2008/098254) discloses thermochemical conversion of cellulose into more readily available carbohydrates, followed by fermentation of the carbohydrates to produce propionic acid. WO2011029166 teaches production of propionic acid using a genetically modified organism such as a *propionibacteria* and a fermentation medium/carbon source such as a monosaccharide, such as glucose. It also mentions inclusion of other "macronutrients," such as nitrogen, and certain specified "micronutrients," that it alleges are required by the organism.

Other references disclose production of propionic acid from a variety of materials, for example, WO2009154624 (glucose); U.S. Pat. No. 5,563,069 (lactose, particularly from whey); Barbirato, F., et al., "Glucose/glycerol co-fermentation: One more proficient process to produce propionic acid by *Propionibacterium acidipropionici*," 1997 *Appl. Microbiol. Biotechnol.* 47, 441-446 (glycerol); Coral, J., et al., "Batch fermentation model of propionic acid production by *Propionibacterium acidipropionici* in different carbon sources," 2008 *Appl. Biochem. Biotechnol.* 151, 333-341 (sugar cane molasses, glycerol and lactate); Choojun, S., et al., "Improvement of propionic acid production for antifungal activity from whey by calcium alginate immobilization of *Propionibacterium acidipropionici* TISTR 442," 2012 *J. Agric. Sci. Tech. A* 2, 863-872 (whey); and Feng, X., et al., "Green and economical production of propionic acid by *Propionibacterium freudenreichii* CCTCC M207015 in plant fibrous-bed bioreactor," 2011 *Bioresour. Technol.* 102, 6141-6146 (cane molasses hydrolysate and hydrolyzed waste *propionibacteria* cells).

While the prior art recognizes that hydrolysates of purified corn and sugar cane syrups are useful in *propionibacteria* fermentations along with necessary and expensive nutrient, vitamin and mineral supplementation, researchers have not heretofore identified ways to reduce or eliminate the need for such supplementation.

The invention provides a process to prepare propionic acid comprising (a) preparing a fermentation broth comprising water; at least 30 weight percent of hydrolyzed corn mash solids, hydrolyzed sugar cane solids, or a combination thereof, based on weight of the fermentation broth as a whole; and *propionibacteria*; wherein supplemental sources of nitrogen, phosphorus, sulfur, iron, manganese, magnesium, calcium, and combinations thereof are not present in total in an amount greater than 0.19 weight percent, based on weight of the fermentation broth as a whole; and wherein supplemental sources of biotin, thiamine, riboflavin, cyanocobalamin, pantothenic acid, and combinations thereof are not present in total in an amount greater than 0.0001 weight percent, based on weight of the fermentation broth as a whole; and (b) allowing the fermentation broth to ferment under conditions suitable to form propionic acid.

Figure 1:
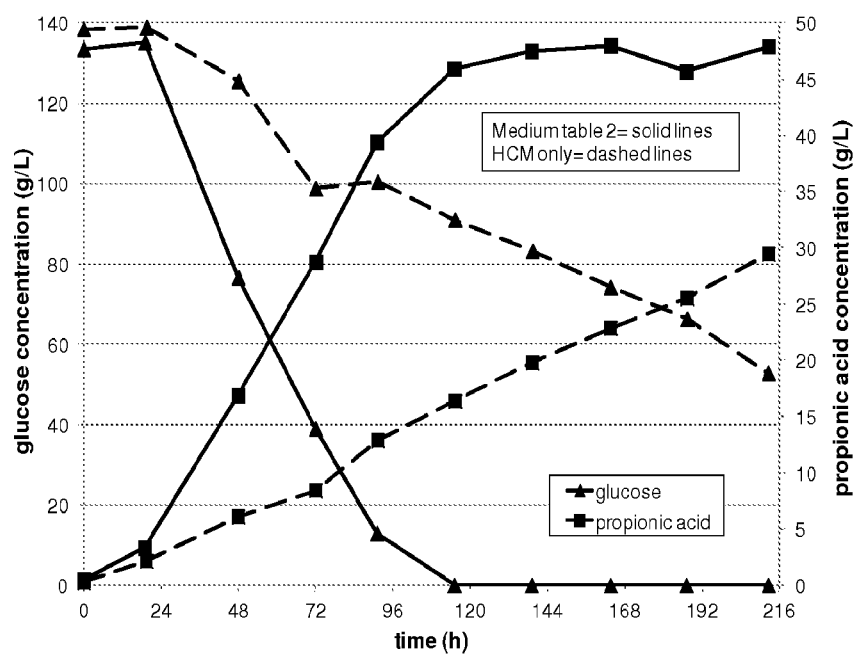
FIG. 1 shows propionic acid and glucose profiles in production fermentations including hydrolyzed corn mash (HCM) medium or medium prepared according to TABLE 2, using identical inoculum from the seed fermentation with medium prepared according to TABLE 1.

The inventive process offers effective production of propionic acid at a cost that is substantially reduced in comparison with fermentation using conventional medium sources such as glucose, glycerol, whey, or C5 or C6 sugars, such as sucrose, that rely on a combination of additional and separate sources of nitrogen; micronutrients such as sulfur and phosphorus; minerals; and vitamins. The cost benefit is derived by using hydrolyzed corn mash solids (HCM), hydrolyzed sugar cane mash solids (EHC), or a combination thereof, as the primary medium source, rather than a more refined primary medium source such as glucose syrup, sucrose from cane sugar or glycerol, in combination with other sources of nitrogen, micronutrients, vitamins and/or minerals, such as inorganic nitrogen sources, protein hydrolysates, yeast, yeast extracts and/or plant grains, to fulfill all of the nutritional requirements of a propionic acid-producing fermentation. The cost benefit is even greater when taking into account the fact that, in fermentations of conventional medium sources, traditional nitrogen, micronutrient, vitamin and mineral supplementation packages are also required for effective fermentation, whereas use of HCM and/or EHC, surprisingly, effectively eliminates the need or preference for any supplementation other than, in some embodiments, cyanocobalamin, which may be optionally employed as an enhancer, but even without which fermentation may still be effectively carried out. Thus, the inventive process is attractive and easily practiced on any scale.

The first starting material is a *propionibacteria*. This may be any species, or combination of species, falling within the *Propionibacterium* genus, but in particularly preferred embodiments it may be *Propionibacteria acidipropionici*. Wild type or genetically-modified *propionibacteria*, or a combination thereof, may be effectively employed. The *propionibacteria* is the basis of the seed culture that may, in some non-limiting embodiments, be first densified via various biomass accumulation steps, and is then used as the basis for the seed fermentation. The seed fermentation then provides the inoculum that is introduced into the production fermentation broth.

The second starting material is the HCM, EHC, or combination thereof. In the present invention it is preferred that, where HCM is selected, the starting, pre-hydrolysis corn mash comprises at least about 80 weight percent (wt %) of starches comprised by or derived from the endosperm of corn kernels, more preferably at least about 90 wt %, and most preferably at least about 95 wt %. In particularly preferred embodiments the pre-hydolysis corn mash comprises at least about 97 wt % of such corn kernel starches. In the case of EHC, the pre-hydrolysis material is sugar cane bagasse, which is the fibrous material remaining after sugar cane stalks are crushed to extract their juice. The bagasse is therefore, by definition, wet, i.e., has a relatively high moisture content that may frequently range from 20 wt % to 50 wt %. Bagasse is very heterogeneous and generally includes approximately 30 wt % to 40 wt % "pith" fibre, derived from the core of the plant, which is mainly parenchyma material. The remainder is "bast", "rind", or "stem" fibre. These are largely derived from sclerenchyma material. For the purpose of the invention, bagasse containing a higher, versus lower, content of cellulose and cellulolignin is generally preferred, though a wide variety of bagasses may be efficacious. In some embodiments of the invention a wide variety of cellulosic sugars may be present in the bagasse. Such sugars may include monosaccharides and oligomers, for example, glucose, xylose, arabinose, and cellobiose, with a total cellulosic sugar content that may range, in some non-limiting embodiments, from 1 wt % to 5 wt %, based upon total weight of bagasse. Another way of looking at this parameter is to determine total grams of cellulosic sugars per liter of bagasse. In certain non-limiting embodiments such monosaccharide and oligomeric cellulosic sugars may range from 15 grams/liter of bagasse (g/L) to 50 g/L.

While pre-hydrolysis mash of either type may be treated in a variety of ways to substantially break down the starches, typical treatments include mechanical milling/grinding processes, which may be combined with or substituted by methods such as, in non-limiting example, contact with enzymes, including an alpha amylase followed by a glucoamylase; contact with acids and/or bases; and other chemical- and thermal-based treatments. These various processes serve to break down the starches that are present in the mash into small sugar-containing polymers and hydrolyze the glycosidic bonds into glucose, thus forming a hydrolyzed mash solids product. For example, in many enzymatic treatments, the alpha amylase breaks the starches into the small sugar containing polymers, while the subsequent exposure to glucoamylase performs the final hydrolysis of the glycosidic bonds. The result of any selected hydrolysis treatment is production of predominantly simple C6 sugars, which serve to support propionic acid production. However, it is important to note that, contrary to conventional understanding and very surprisingly, the HCM and/or EHC provides, as a primary medium source, not only the simple C6 sugars, but also the nitrogen, micronutrients, minerals, and vitamins needed for desirably effective fermentation.

The third starting material is water. This may be, for example, any industrial process water, including but not limited to potable water or other water. Reasonable freedom from contaminants such as chemicals, metals and the like is desirable, but because of sterilization of the combination of HCM and/or EHC and water prior to addition of the *propionibacteria* in the production fermentation medium, freedom from live biocontamination is generally not critical. The presence of any other constituents, generally in parts per million (ppm) proportion, including but not limited to impurities contained in the constituents as purchased or otherwise obtained, residues and particulates from processing equipment, and the like, may also be tolerated, provided their presence does not alter the results of the process in any measurable and/or undesirable and significant way.

The production fermentation medium may be varied over a wide range of proportions of the three starting components, except as indicated otherwise hereinbelow. The primary medium source, the HCM and/or EHC, may be most conveniently obtained or prepared such that such is initially a solution that is approximately 60 weight percent (wt %) to 70 wt % mash solids, and therefore includes from 30 wt % to 40 wt % water. This precursor solution is then combined with additional water in the production fermentation medium such that the mash solids range from 30 wt % up to 99 wt %, preferably from 30 wt % to 80 wt %, and most preferably from 60 wt % to 70 wt %, based on the production fermentation medium, i.e., fermentation broth, as a whole.

Once the HCM and/or EHC have been combined with water to form a pre-production fermentation solution, it is desirable to sterilize the solution via procedures such as steam-in-place processes, such that any organisms therein do not undesirably interfere with the *propionibacteria*'s growth and function to produce propionic acid. The timing of this sterilization step thus avoids destruction/decomposition of the *propionibacteria* due to thermal effects and helps to ensure optimal *propionibacteria* fermentation by eliminating any competing bacterial species.

It is preferred that the *propionibacteria* seed culture be densified prior to inclusion as the inoculum in the production fermentation medium. In particular embodiments it is desirable that the seed culture exhibits an optical density at 600 nanometers ($OD_{600}$) of at least 5, preferably at least 10, and more preferably at least 20. Assuming an inoculum has an $OD_{600}$ of at least 5, it is preferred that it be added to the production fermentation medium in an amount ranging from 1 wt % to 60 wt %, more preferably from 3 wt % to 15 wt %, and most preferably from 5 wt % to 10 wt %, based on combined weight of the water and HCM and/or EHC. Those skilled in the art will be aware that, while an inoculum having an $OD_{600}$ of less than 5 may be selected, use of such will generally increase overall fermentation time to reach a target level of propionic acid production in comparison with use of a higher $OD_{600}$ inoculum.

A particular feature and advantage of the invention is that an effective fermentation may be carried out when substantially all of the medium source is HCM and/or EHC. This means that production fermentation using *propionibacteria* may be effectively carried out in the substantial absence of any other nitrogen source, any other micronutrient source, any other mineral source, and any other vitamin source. The phrase "any other nitrogen source" as used herein is thus defined to mean any supplemental source(s) of nitrogen (e.g., proteins, amino acids, or other inorganic/organic nitrogen containing materials). The phrase "any other micronutrient source" as used herein is thus defined to mean any supplemental source(s) of sulfur and/or phosphorus. The phrase "any other mineral source" refers to any supplemental source(s) including at least one of iron, manganese, magnesium, and/or calcium. The phrase "any other vitamin source" refers to any supplemental source(s) including at least one of biotin, riboflavin, thiamine, pantothenic acid, and/or cyanocobalamin. It is noted that "any other" thus means "any supplemental source" of one or more members of these groupings.

"Substantial absence" with respect to the supplemental sources denominated hereinabove means that the fermentation production medium, i.e., fermentation broth, does not include, added as a thereto, an amount of the indicated source that is, in total, greater than 0.19 wt %, preferably not greater than 0.1 wt %; and more preferably not greater than 0.01 wt %. "Substantial absence" with respect to any supplemental source of vitamins means that the fermentation broth most preferably does not include vitamin sources, in total, in an amount greater than 0.0001 wt % (1 milligram per liter (mg/L)). These percentages are based on weight of the production fermentation medium as a whole.

Because vitamin/mineral packages and, particularly, nitrogen and micronutrient sources may represent a significant portion of the cost of most conventional propionic acid-producing fermentations, the surprising reduction in need for such supplementation offered by the selection of HCM and/or EHC as a primary medium source offers a significant savings. However, in some embodiments cyanocobalamin supplementation may be desirable, as it may significantly enhance propionic acid production in the inventive HCM and/or EHC-based fermentations. Such supplementation is preferably in an amount of at least 0.00001 wt % (0.1 mg/L) of cyanocobalamin (a vitamin source which is a vitamin B12 precursor, i.e., a vitamer), preferably from 0.0001 wt % (1 mg/L) to 0.0003 wt % (3 mg/L), and more preferably from 0.00015 wt % (1.5 mg/L) to 0.00025 wt % (2.5 mg/L).

It is noted that one or more other carbon sources, such as, e.g., sugars, carbohydrates, cellulosics, or other organic carbon containing materials, alternatively termed "non-HCM/EHC solids", may also be included in the fermentation production medium, along with the HCM and/or EHC solids, in an amount from 1 wt % to 69 wt % solids, based on weight of the production fermentation medium as a whole. Preferably this non-HCM/EHC solids content is from 1 wt % to 40 wt %, more preferably from 1 wt % to 20 wt %, and most preferably from 1 wt % to 10 wt %, on the same basis. However, carbon sources are categorized herein as medium sources and thus, if such also contribute nitrogen, the specified micronutrients, the specified vitamins, and/or the specified minerals, are considered to also be supplemental sources thereof. Nonetheless, it is important to note that there is, in particular embodiments, no need for any other carbon (medium) sources, and fermentation based on a medium that is all-HCM, all-EHC or all-combination medium, or alternatively a near-all-HCM and/or EHC medium, may be effectively carried out on a variety of scales.

Fermentation of the defined production fermentation medium, i.e., fermentation broth, may be accomplished under any conditions suitable to form propionic acid. In general such conditions may include a temperature that preferably ranges from 25° C. to 50° C., more preferably from 30° C. to 40° C., most preferably from 30° C. to 34° C.; a time preferably ranging from 10 hours (h) to 200 hours (h), more preferably from 60 to 120 and most preferably from 80 to 100 hours (h); an applied (gauge) pressure (i.e., in addition to any hydrostatic pressure that may be generated) preferably ranging from 0 kilopascals (kPa) to 10,000 kPa, more preferably from 500 kPa to 2000 kPa, and most preferably from 100 kPa to 150 kPa; a pH preferably ranging from 3 to 7.5, more preferably from 4 to 7, and most preferably from 6.25 to 6.75; and overlay nitrogen in the headspace of the fermentation vessel at 0.1 gas volume flow per unit of liquid volume per minute (vvm) to 1 vvm, more preferably from 0.1 vvm to 0.5 vvm, and most preferably from 0.2 vvm to 0.4 vvm. Fermentation is complete when maximum productivity plateaus, which will vary according to the sum of conditions. Those skilled in the art will be aware of how these factors may be effectively varied in order to generate desired levels of propionic acid production within desirable and/or industrially acceptable time limits.

In certain particular embodiments yield of the inventive process, in terms of grams of glucose consumed per gram of propionic acid produced (g/g), may be at least 0.3 g/g, preferably at least 0.35 g/g, more preferably at least 0.36 g/g, and most preferably at least 0.5 g/g. In certain embodiments the propionic acid production may also be defined as being at least 30 wt %, preferably at least 50 wt %, more preferably at least 60 wt %, and most preferably at least 70 wt %, in terms of g/g, when compared with propionic production, under otherwise identical conditions and equivalent glucose amount in g/L, in a glucose-based fermentation medium which requires additional medium sources to supplement the nitrogen, micronutrients, vitamins and minerals as such are identified hereinabove.

EXAMPLE 1 AND COMPARATIVE EXAMPLE A

1. Seed Culture a. Seed Culture Medium Preparation

For medium in seed train bottles, a base propionic acid medium (PAM), 1.5 L, is prepared using 10 grams per liter (g/L) yeast extract, 5 g/L trypticase soy, 0.25 g/L $K_2HPO_4$, and 0.056 g/L $MnSO_4.H_2O$. The seed train medium is supplemented, post-sterilization, with 40 g/L glucose.

The base PAM is made in concentrated form to accommodate the additive volume from the separately sterilized glucose solution. The concentrated glucose solution is made at 500 g/L by diluting 55 g of glucose monohydrate to a total 100 mL volume. The glucose solution (100 mL) is stoppered and then sealed in a 125 mL serum bottle. The 1.5 L of base PAM is prepared in a 2 L bottle as shown in TABLE 1 without glucose (total volume is 1380 mL prior to glucose addition) and is then purged with nitrogen for approximately 15 min with a steady flow of nitrogen, while stirring.

The PAM is then aliquoted into serum bottles at a final volume of 46 mL for the seed train. An amount, 920 mL, of PAM in a 2 L sealed bottle is used as the final seed train step. The PAM and glucose solutions are sterilized separately by treatment in an autoclave for 30 min at 121° C. and 15 psig (101 kPa). Immediately after sterilization, the headspace of all serum bottles is purged free of oxygenated air with sterile nitrogen for 4 min. Once cooled, the glucose solution is added aseptically via syringe to the concentrated medium solution (e.g., 4 mL of glucose solution is added to the serum bottle base PAM and 80 mL of glucose solution is added to 920 mL of base PAM). After glucose addition the inoculation bottle is purged 30 min through the stirred medium with sterile nitrogen.

b. Seed Culture Preparation

The *propionibacteria* cultures for the following examples and comparative examples are initiated by thawing a cryogenically stored wild type *Propionibacteria acidipropionici* culture (stored at −80° C., 15% volume per volume (v/v) glycerol, optical density measured at 600 nanometers ($OD_{600}$)=0.5) on ice. Anaerobically, 300 microliters (A) of the thawed culture is transferred via syringe into a serum bottle containing 50 mL of PAM supplemented with 40 g/L glucose in a 125 mL serum bottle. This 50 mL inoculated culture is incubated statically at 32° C. and is called the Stage 1 seed train culture. After approximately 24 h ($OD_{600}$=0.5), 8 mL of the culture is transferred into Stage 2, which is 1 L of PAM in a 2 L bottle. This 1 L Stage 2 culture is incubated under identical conditions to Stage 1 for 24 h to achieve an $OD_{600}$=0.5. The mature Stage 2 culture is then transferred to the seed fermentation step described hereinbelow to build cell density.

2. Seed Fermentation a. Seed Fermentation Medium Preparation

Seed fermentation medium is prepared with the constituents shown in TABLE 1. First, a concentrated glucose solution is made in an amount of 717 g/L. The glucose solution is sterilized by treatment in an autoclave for 30 min at 121° C. and 15 psig (101 kPa) in 5 L stainless steel cans. The remaining constituents shown in TABLE 1 are first added individually to the bioreactor. The seed fermentation medium as a whole, with the exception of the glucose solution, is sterilized in the bioreactor for 30 min at 121° C. with a temperature ramp of approximately 10° C./min. The separately sterilized glucose solution is then charged to the bioreactor.

TABLE 1

Seed fermentation medium recipe

| Item Name | Amount/L |
| --- | --- |
| Yeast extract | 10 g |
| Trypticase soy broth | 5 g |
| Potassium phosphate dibasic | 0.25 g |
| Manganese sulfate monohydrate | 0.056 g |
| Glucose* | 100 g |

*Glucose (717 g/L) is made from the monohydrate and sterilized separately prior to mixing with other constituents.

3. Production Fermentation a. Production Fermentation Medium Preparation

Two different production fermentation mediums are prepared. Both are inoculated from a seed employing the seed fermentation medium from TABLE 1. In the first, which is Example 1, an amount of HCM, estimated at about 40 wt % by weight of HCM solids plus water, having a glucose content equivalent to 135 g/L, is employed with no other additives. In the second, which is Comparative Example A, laboratory grade glucose is employed in the same amount (135 g/L), along with the additional constituents shown in TABLE 2, representing a conventional fermentation medium. Both the yeast extract and trypticase soy broth are complex nitrogen sources that are known to those skilled in the art to contain a variety of vitamins and minerals, but no assay thereof is available.

TABLE 2

Production fermentation medium recipe for Comparative Example A

| Item Name | Amount/L |
| --- | --- |
| Yeast extract | 10 g |
| Trypticase soy broth | 5 g |
| Potassium phosphate dibasic | 0.25 g |
| Manganese sulfate monohydrate | 0.056 g |
| Glucose | 135 g |

Fermentations are carried out for both Example 1 and Comparative Example A under the following standardized conditions: a 30-L bioreactor, with a media volume of 15 L, a temperature of 32° C., agitation 300 revolutions per minute (rpm), nitrogen stream at 3.5 standard liters per minute (slpm) (i.e., 0.23 vvm (volume gas per volume medium per minute)) over the headspace, pH control at 6.5 with addition of 15 molar (M) ammonium hydroxide, and pressure set at 1100 mBar (110 kPa). The two different production fermentation mediums are then analyzed by liquid chromatography (LC) for propionic acid and the results are shown in FIG. 1. The results demonstrate that utilizing only the diluted HCM results in significant rate and yield of propionic acid, compared with the results using laboratory grade glucose and additives as indicated in TABLE 2. In fact, at 91 hours, while productivity using only HCM is only about 33 percent, i.e., reduced to approximately one-third, compared to productivity using the conventional medium with laboratory grade glucose including the TABLE 2 additives (see TABLE 3), it is estimated that the cost of that production, in terms of US dollars per kilogram of propionic acid produced, is reduced to approximately one-thirtieth, i.e., by about 30-fold. Thus, the Example 1 process is far more economically attractive. Furthermore, although productivity is reduced in the Example 1 process in comparison with the Comparative Example A process, fermentation yield is comparable, at 0.37 grams of glucose consumed per gram of propionic acid produced (g/g) for fermentation on glucose and 0.36 g/g for fermentation on HCM. Both processes also produce acetic, lactic, and succinic acids in significant amounts.

TABLE 3

Productivity and titer for different production fermentation mediums

| | Propionic Acid at 91 h | |
| --- | --- | --- |
| Production Fermentation | Productivity (g/L/h) | Titer (g/L) |
| Comparative Example A | 0.43 | 39 |
| Example 1 | 0.14 | 13 |

EXAMPLE 2 AND COMPARATIVE EXAMPLE B

Comparative studies illustrate the effects of inclusion versus absence of various supplemental vitamins. Production fermentation mediums, designated as Example 2 and Comparative Example B, are prepared according to Example 1 and Comparative Example A in 30-L bioreactors, except that glucose is measured by liquid chromatography (LC), pre-sterilization, and standardized for each at approximately 125 g/L by water additions to the medium. Each of the fermentation mediums is then sterilized by steam-in-place technology for 30 min at 121° C., with a temperature ramp of approximately 10° C./min. Sterile tap water is then added to a 13.5 L pre-inoculation volume, noting that additional adjustment is made to subtract for additive volume from vitamin supplementation for Comparative Example B.

Figure 2:
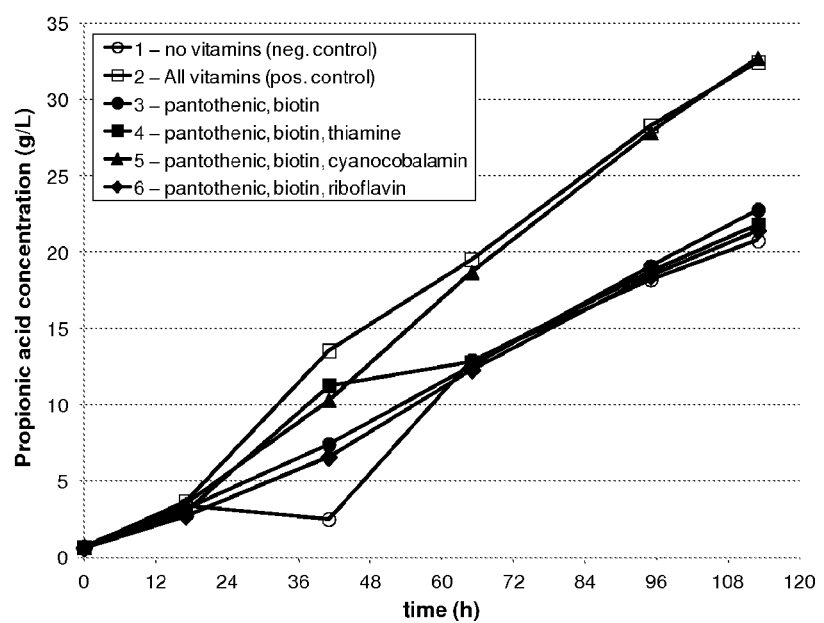
FIG. 2 shows production fermentation kinetic profiles for HCM with differential vitamin supplementation of the production fermentation medium.

Vitamins are selected based on literature precedent for *propionibacteria* growth requirements. The Example is represented as a single variable modification experiment wherein five vitamins are variously subtracted from the additive package to determine the effect of each vitamin on production of propionic acid. Vitamin solutions containing five or fewer of the five vitamins (specified hereinbelow) are independently made immediately prior to inoculation. This is carried out beginning with a standard vitamin additive package, comprised of riboflavin, pantothenic acid, biotin, thiamine and cyanocobalamin, employed at a final fermentation concentration of 2 ma each. A stock is made at 100 mg/L, adjusted to pH=7 with dilute (approximately 0.1 M) sodium hydroxide in one solution, and sterilized by passage through a 0.22 micrometer (μm) filter. Appropriate amounts of the 100 ma solution are added to the identified HCM reactors to incorporate the desired vitamin or vitamins and normalize fermentation dilution. Each additive or additive package is then dosed to the production fermentation medium, i.e., fermentation broth, aseptically through a bottle with steam sterilizable connection. Productivity results of fermentations including the individual vitamins are shown in FIG. 2.

While it is clear that the vitamin mixture (all included vitamins) increases productivity of propionic acid, the differential vitamin addition experiments determine that cyanocobalamin is a particularly significant additive. Increasing the vitamin source amount above 2 mg/L and additional dosing later in the fermentation does not further improve the propionic acid production.

EXAMPLE 3

Figure 3:
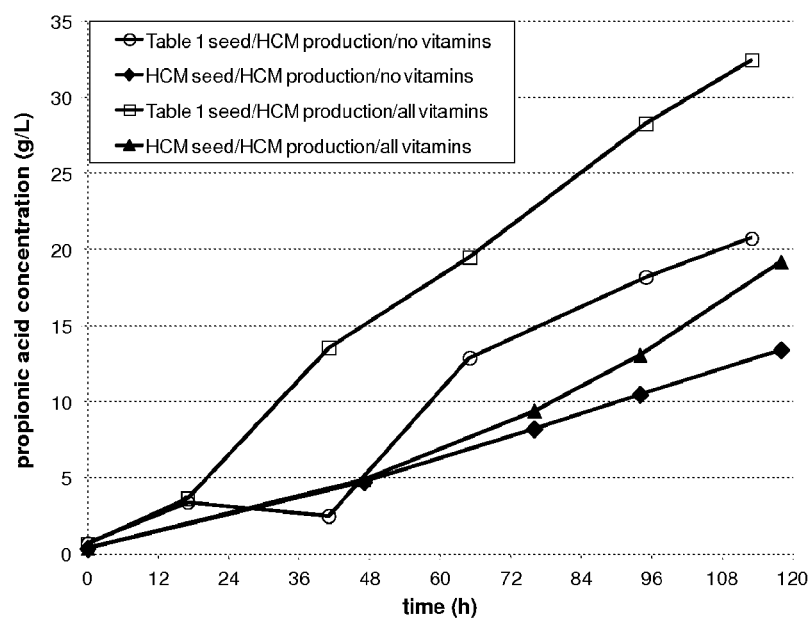
FIG. 3 shows fermentation kinetic profiles for all-HCM production fermentations with and without five-vitamin supplementation, using independent inoculum from seed fermentations based on either the medium prepared according to TABLE 1 or an all-HCM medium.

Experimentation is done to determine whether an all-HCM seed fermentation, followed by an all-HCM production fermentation, results in significant propionic acid production. Four examples show all-HCM production fermentations preceded by seed fermentations corresponding to TABLE 1 or all-HCM seed fermentation mediums, two with no vitamins added and two with all vitamins added at the production fermentation step. Conditions correspond to those of earlier Examples and Comparative Examples. The results, recorded in FIG. 3, illustrate that even inoculums prepared from seed cultures grown on pure HCM produce significant levels of propionic acid in an all-HCM production fermentation, with or without vitamins added during the production fermentation.

EXAMPLE 4 AND COMPARATIVE EXAMPLE C

Figure 4:
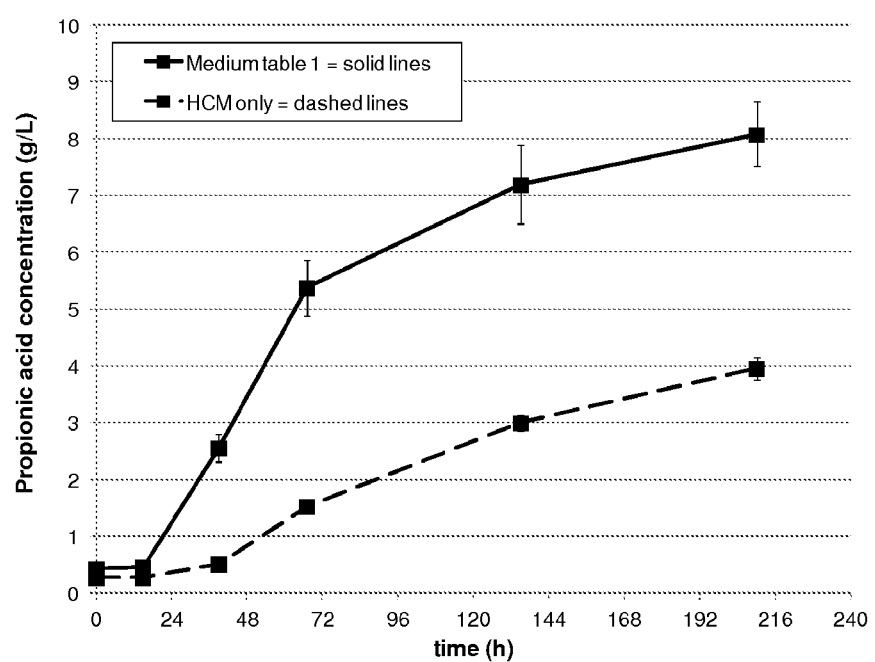
FIG. 4 shows a fermentation profile for an all-HCM fermentation without using ammonia for pH control, based on an HCM seed fermentation inoculums, in comparison with a fermentation profile for a fermentation based on an inoculums using medium prepared according to TABLE 1.

Serum bottle fermentations with pure HCM medium, absent of any medium supplementation, are conducted in triplicate. The results indicate that pure HCM, even without the addition of ammonium hydroxide for pH control (as employed in Example 1), can produce significant levels of propionic acid. Furthermore, since these fermentations are conducted in completely sealed serum bottles, this experiment demonstrates that HCM alone contains all the nutrients required by *Propionibacterium* to grow and produce propionic acid at significant levels. FIG. 4 shows a comparison of an all-HCM fermentation (dashed line, Example 4) compared with fermentation on the medium of TABLE 1, with the exception of a 40 g/L starting glucose concentration (solid line, Comparative Example C), over a time of 216 hours.

EXAMPLE 5

Two sets of pretreated and hydrolyzed sugar cane bagasse samples are fermented for propionic acid production. In both sets, sugar cane bagasse is first hydrothermally pretreated at high temperature (185° C. to 195° C.) and pressure greater than atmospheric (101,325 Newtons per square meter, $N/m^2$), releasing a slurry of solubilized hemicellulose and solid lignocellulosic material. For the enzymatic hydrolysis of the first set, the pH of the whole slurry is adjusted to 4.8 with aqueous ammonium hydroxide and then an enzyme cocktail containing cellobiohydrolases, endoglucanases, xylanases and beta-glucosidases is added at 10 filter paper activity units (FPU) per gram of total solids in the mixture. Hydrolysis is then performed at 50° C. for 48 h under orbital stirring to produce enzymatically hydrolyzed sugar cane solids (EHC) in a water solution. In the second set of samples, the described pretreatment is performed and the resulting lignocellulosic material is separated from the liquid fraction (which contains mainly solubilized hemicellulose) using an agitated Nutsche filter (ANF). The recovered solids are washed 3 times in the filter using 45 kg of water per 15 kg of input bagasse to minimize the presence of potential remaining fermentation inhibitors such as furfural, hydroxymethylfurfural and acetic acid. The material is then hydrolyzed using an identical method to the first set of samples to produce enzymatically hydrolyzed sugar cane solids (EHCW).

The directly hydrolyzed and washed hydrolyzed samples are then split. One aliquot of each is fermented directly without further modification. In the second aliquot, 7.5 mL of piperazine-N,N'-bis(ethane-sulfonic acid) ("PIPES") buffer is added, post-sterilization, at a final 0.25 M concentration to both the washed and unwashed hydrolysis samples to stabilize pH during fermentation.

Each sample is fermented in triplicate in a 125 mL terminally sealed serum bottle. 50 mL (or 42.5 mL where using PIPES) of sample is aliquoted to each serum bottle before autoclaving at 121° C. for 30 minutes. The sample pH of all samples ranges from 6.0-7.0 prior to autoclaving. However, after autoclaving the pH of all samples falls to 4.0-5.0 and requires adjustment with 1 M NaOH to return the pH to 6.0-7.0. After pH adjustment, each sample is inoculated with 300 μL of PAM culture grown for ~24 hours to an $OD_{600nm}$ of 0.5. After inoculation, fermentations are maintained at 32° C. without agitation. Samples are then collected periodically to assay for propionic acid production.

Figure 5:
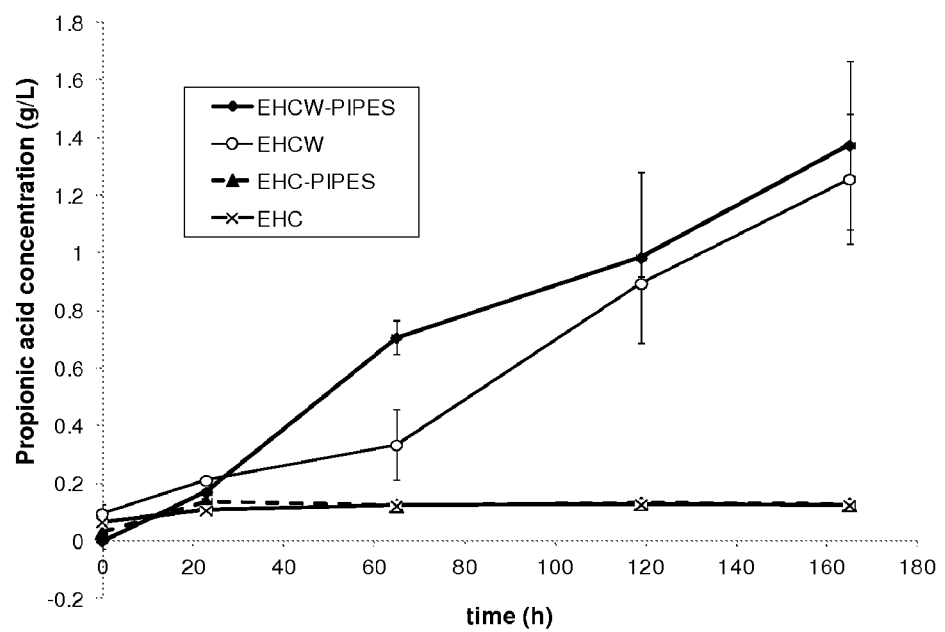
FIG. 5 shows propionic acid profiles for fermentation based on medium prepared from four enzymatically hydrolyzed (sugar) cane (EHC) samples.
Figure 6:
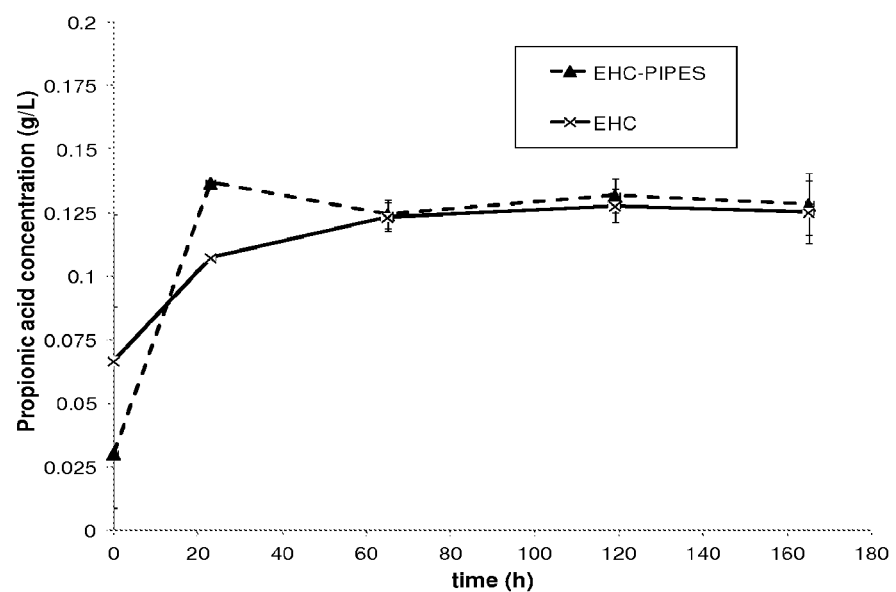
FIG. 6 shows propionic acid profiles for fermentation based on medium prepared from two unwashed EHC samples.

The data in FIG. 5 below demonstrates that an appreciable amount of propionic acid can be produced directly from hydrolyzed sugar cane samples without any supplementation. Thus, pure EHC contains sufficient nutrients for propionic acid production. Washing the EHC samples as described above significantly improves performance as shown in FIG. 5, but even unwashed EHC makes a significant amount of propionic as shown in FIG. 6. Supplementation with PIPES buffer improves performance, but even without PIPES buffering, a significant amount of propionic acid is produced.

SAMPLE ABBREVIATIONS

EHC—Enzymatically hydrolyzed sugar cane solids
EHCW—Washed enzymatically hydrolyzed sugar cane solids
EHC PIPES—Enzymatically hydrolyzed sugar cane solids with PIPES buffering EHCW PIPES—Washed enzymatically hydrolyzed sugar cane solids with PIPES buffering FIG. 5 shows propionic acid profiles for fermentation based on medium prepared from four enzymatically hydrolyzed (sugar) cane (EHC) samples.

FIG. 6 shows propionic acid profiles for fermentation based on medium prepared from two unwashed EHC samples.

What is claimed is:

1. A process to prepare propionic acid comprising:
   (a) contacting corn mash solids, sugar cane mash solids, or a combination thereof with an acid to produce pre-hydrolyzed corn mash solids, pre-hydrolyzed sugar cane mash solids, or a combination thereof;
   (b) hydrolyzing said pre-hydrolyzed corn mash solids, said pre-hydrolyzed sugar cane mash solids, or said combination thereof to produce hydrolyzed corn mash solids, hydrolyzed sugar cane mash solids, or a combination thereof;
   (c) preparing a fermentation broth comprising water; at least 30 weight percent of said hydrolyzed corn mash solids said hydrolyzed sugar cane mash solids, or said combination thereof, based on weight of said fermentation broth as a whole;
   and *propionibacteria*;
   wherein supplemental sources of nitrogen, phosphorus, sulfur, iron, manganese, magnesium, calcium, and combinations thereof are not present in total in an amount greater than 0.19 weight percent, based on the weight of said fermentation broth as a whole;
   wherein supplemental sources of biotin, thiamine, riboflavin, cyanocobalamin, pantothenic acid, and combinations thereof are not present in total in an amount greater than 0.0001 weight percent, based on weight of said fermentation broth as a whole;
   (d) fermenting said fermentation broth under suitable conditions to produce propionic acid.

2. The process of claim 1, wherein said *propionibacteria* is selected from wild type and genetically-modified *propionibacteria*, and combinations thereof.

3. The process of claim 2, wherein said *propionibacteria* is selected from wild type and genetically-modified *Propionibacteria acidiprionici*.

4. The process of claim 1, wherein said corn mash solids comprise at least 80 weight percent of corn kernel starches prior to hydrolysis.

5. The process of claim 2, wherein said sugar cane mash solids comprise at least 1 weight percent of cellulosic monosaccharides and oligomers prior to hydrolysis.

6. The process of claim 1, wherein said suitable conditions include at least one of a temperature ranging from 25° C. to 50° C.; a time ranging from 10 hours to 200 hours; an applied pressure ranging from 0 kilopascals to 1000 kilopascals; a pH ranging from 3 to 7.5; and overlay of nitrogen ranging from 0.1 gas volume flow per unit of liquid volume per minute to 1 gas volume flow per unit of liquid volume per minute.

7. The process of claim 1, wherein said fermentation broth further comprises at least one carbon source, other than said hydrolyzed corn mash solids or said hydrolyzed sugar cane mash solids or said combination thereof, in an amount from 1 weight percent to 69 weight percent, based on the weight of said fermentation broth as a whole.

8. The process of claim 7, wherein said fermentation broth further comprises at least one carbon source, other than said hydrolyzed corn mash solids or said hydrolyzed sugar cane solids or said combination thereof, in an amount from 1 weight percent to 40 weight percent, based on the weight of said fermentation broth as a whole.

9. A process to prepare propionic acid comprising:
   (a) contacting sugar cane mash solids with an acid to produce pre-hydrolyzed sugar cane mash solids;
   (b) hydrolyzing said pre-hydrolyzed sugar cane mash solids to produce hydrolyzed sugar cane mash solids;
   (c) preparing a fermentation broth comprising water; at least 30 weight percent of said hydrolyzed sugar cane mash solids, based on weight of said fermentation broth as a whole;
   and *propionibacteria*;
   wherein supplemental sources of nitrogen, phosphorus, sulfur, iron, manganese, magnesium, calcium, and combinations thereof are not present in total in an amount greater than 0.19 weight percent, based on the weight of said fermentation broth as a whole;
   wherein supplemental sources of biotin, thiamine, riboflavin, cyanocobalamin, pantothenic acid, and combinations thereof are not present in total in an amount greater than 0.0001 weight percent, based on weight of said fermentation broth as a whole;
   (d) fermenting said fermentation broth under suitable conditions to produce propionic acid.

10. The process of claim 9, wherein said *propionibacteria* is selected from wild type and genetically-modified *propionibacteria*, and combinations thereof.

11. The process of claim 10, wherein said *propionibacteria* is selected from wild type and genetically-modified *Propionibacteria acidiprionici*.

12. The process of claim 9, wherein said sugar cane mash solids comprise at least 1 weight percent of cellulosic monosaccharides and oligomers prior to hydrolysis.

13. The process of claim 9, wherein said suitable conditions include at least one of a temperature ranging from 25° C. to 50° C.; a time ranging from 10 hours to 200 hours; an applied pressure ranging from 0 kilopascals to 1000 kilopascals; a pH ranging from 3 to 7.5; and overlay of nitrogen ranging from 0.1 gas volume flow per unit of liquid volume per minute to 1 gas volume flow per unit of liquid volume per minute.

14. The process of claim 9, wherein said fermentation broth further comprises at least one carbon source, other than the hydrolyzed sugar cane mash solids, in an amount from 1 weight percent to 69 weight percent, based on the weight of said fermentation broth as a whole.

15. The process of claim 14, wherein the fermentation broth further comprises at least one carbon source, other than the hydrolyzed sugar cane mash solids, in an amount from 1 weight percent to 40 weight percent, based on the weight of said fermentation broth as a whole.

* * * * *